United States Patent

Wilson et al.

Patent Number: 5,954,720
Date of Patent: Sep. 21, 1999

[54] BIPOLAR ELECTROSURGICAL END EFFECTORS

[75] Inventors: Jeff A. Wilson, Mendon, Mass.; James R. Young, Ft. Lauderdale; John K. Danks, Delray Beach, both of Fla.

[73] Assignee: Endoscopic Concepts, Inc., Del Ray Beach, Fla.

[21] Appl. No.: 08/942,133

[22] Filed: Oct. 1, 1997

Related U.S. Application Data

[60] Provisional application No. 60/029,405, Oct. 28, 1996.

[51] Int. Cl.$^6$ .................................................. A61B 17/39
[52] U.S. Cl. ................................ 606/50; 606/46; 606/48; 606/51; 606/170; 606/174
[58] Field of Search ................................ 606/45, 46, 48, 606/49, 50, 51, 52, 170, 174

[56] References Cited

U.S. PATENT DOCUMENTS

| | | | |
|---|---|---|---|
| 3,920,021 | 11/1975 | Hiltebrant | 606/51 |
| 4,005,714 | 2/1977 | Hiltebrant | 606/51 |
| 5,171,256 | 12/1992 | Smith et al. | 606/205 |
| 5,258,006 | 11/1993 | Rydell et al. | 606/205 |
| 5,330,471 | 7/1994 | Eggers | 606/48 |
| 5,342,381 | 8/1994 | Tidemand | 606/174 |
| 5,356,408 | 10/1994 | Rydell | 606/48 |
| 5,391,166 | 2/1995 | Eggers | 606/48 |
| 5,396,900 | 3/1995 | Slater et al. | 128/751 |
| 5,472,443 | 12/1995 | Cordis et al. | 606/48 |
| 5,540,685 | 7/1996 | Parins et al. | 606/51 |
| 5,569,243 | 10/1996 | Kortenbach et al. | 606/46 |
| 5,573,534 | 11/1996 | Stone | 606/48 |
| 5,766,166 | 6/1998 | Hooven | 606/45 |
| 5,779,701 | 7/1998 | McBrayer et al. | 606/48 |

FOREIGN PATENT DOCUMENTS

| | | | |
|---|---|---|---|
| 2680314 | 2/1993 | France | 606/51 |

*Primary Examiner*—Lee Cohen
*Attorney, Agent, or Firm*—Miller & Martin LLP

[57] ABSTRACT

A novel, bipolar, electrosurgical instrument is provided with one metal and one ceramic end effector. Current is passed through the metal end effector and through an insulated conduit to the distal tip of the ceramic end effector. A connection at the distal tip of the ceramic end effector allows the current to return along exposed conductive strip which is spaced apart from the metal end effector in cutting action by a gap of approximately 0.020 inches when the ceramic and metal blade supports are brought into contact with tissue, a current flows from the exposed metal strip on the ceramic blade through to the metal blade thereby effecting cauterization, preferably slightly in advance or at the point of cutting between the ceramic and metal blades.

20 Claims, 7 Drawing Sheets

BIPOLAR ELECTROSURGICAL END EFFECTORS

BACKGROUND OF THE INVENTION

This application claims the benefit of U.S. provisional application no. 60/029,405 filed Oct. 28, 1996.

The present invention relates to endoscopic surgical instruments, and more particularly to instruments known as end effectors which may include cutters or scissors, graspers and dissectors which are useful in laparoscopic or endoscopic procedures. The surgical instruments made according to the present invention are bipolar to permit safe and effective dissection, incising and cauterization of blood vessels, bleeding tissues, or non-bleeding tissues.

The use of heat for the cauterization of bleeding wounds dates back for centuries. More recently, the use of radio frequency (RF) electrical current traveling through a portion of the body has been widely used to stop bleeding. The RF energy cauterizes the blood by heating the blood proteins to a temperature where those proteins congeal similarly to the process involved in the cooking of egg whites. RF energy is preferred because its frequency is above that which could otherwise cause neuromuscular stimulation. The most frequently used modes of RF cauterization are monopolar and bipolar coagulation.

In monopolar coagulation, an active electrode is applied to a bleeding site and the electrical current flows from the electrode through the patient's body to a return electrode which may be a conductive plate in electrical contact with a large surface area of the patient's body such as the buttocks or thigh. One technique in which the monopolar mode may be employed involves fulguration which is the use of a spark or arc from the active electrode to the tissue.

Bipolar devices include both the active and return electrodes. Thus the electrical current flows down the surgical instrument to the active electrode and typically crosses a space on the order of millimeters to the return electrode and returns through the surgical device. Because no separate return electrode is required, bipolar electrical surgical devices have the inherent advantage of containing the RF energy in a defined area. This prevents potential patient complications related to monopolar RF energy traveling through the patient's body, such as the burning of nearby tissue or affecting the visceral function. The reduction of patient complications is also accomplished because bipolar devices typically require less RF energy than equivalent monopolar devices.

Endoscopic surgical instruments, such as the bipolar electrosurgical end effectors are often used in laparoscopic surgery, which is most commonly employed for cholecystectomies (gall bladder), hysterectomies, appendectomies, and hernia repair. These surgeries are generally initiated with the introduction of a Veress needle into the patient's abdominal cavity. The Veress needle has a stylet which permits the introduction of gas into the abdominal cavity. After the Veress needle is properly inserted, it is connected to a gas source and the abdominal cavity is insufflated to an approximate abdominal pressure of 15 mm Hg. By insufflating the abdominal cavity, a pneumoperitoneum is created separating the wall of the body cavity from the internal organs.

A surgical trocar is then used to puncture the body cavity. The piercing tip or obturator of the trocar is inserted through the cannula or sheath and the cannula partially enters the body cavity through the incision made by the trocar. The obturator can then be removed from the cannula and an elongated endoscope or camera may be inserted through the cannula to view the body cavity, or surgical instruments such as bipolar electrosurgical end effectors according to the present invention, may be inserted to perform the desired procedure.

Frequently an operation using trocars will require three or four punctures so that separate cannula are available for the variety of surgical instruments which may be required to complete a particular procedure. As described in U.S. Pat. No. 5,258,006 for bipolar electrosurgical forceps, the alternatives to bipolar cauterization or coagulation have been unacceptable. Monopolar instruments, using RF energy, require greater current and unpredictabilities in current flow may have a destructive effect on tissues surrounding the area to be cauterized.

While non-contact positioning of a laser may overcome this shortcoming, the laser has no way of holding a bleeding vessel and is not used on large bleeders. Laser based cauterization instruments remain expensive and unsuitable for tissue dissection techniques other than cauterization, such as blunt dissection or sharp dissection. Laser cauterization instruments suffer from the additional shortcomings that it is difficult to control the depth of penetration of the laser energy and that non-contact positioning of a laser can permit the laser beam to reflect off of other instruments and cause damage to surrounding tissue.

Furthermore, as described in U.S. Pat. No. 5,472,443 for an electrosurgical apparatus, there have been difficulties in bipolar instruments in two primary areas. The first is the difficulty in preventing excessive trauma or charring to the tissue being cauterized. Such charring or tissue damage can impede healing and regrowth of tissue. In addition, bipolar instruments suffer from a buildup of coagulated blood or severed tissue. In prior art instruments, such buildup could impede the effectiveness of the cauterization action of the instrument, and also tends to cause previously cauterized tissue to adhere to the coagulated blood and tissue on the instrument resulting in possible tears and reopening of blood flows along the cut or incision. The invention described herein overcomes both of these shortcomings and may effectively reduce the number of surgical instruments required for a given procedure.

SUMMARY OF THE INVENTION

It is therefore an object of the invention to provide an improved surgical instrument with bipolar end effectors.

It is an additional object of the invention to provide bipolar end effectors wherein one end effector is metal and the other is ceramic with a conducting strip.

It is a further object of the invention to pass current through the conducting strip of the ceramic end effector so that the coagulation caused by the RF energy tends to be very slightly in advance of or at the cutting point between the metal and ceramic end effectors, rather than rearward of the cutting point.

It is yet a further object of the invention to provide a bipolar instrument which utilizes RF energy more efficiently to cauterize tissue and thereby minimize charring of tissue.

It is still a further object of the invention to provide for the flow of RF energy exposed to tissue rearward from the end effector portion of the surgical instrument toward the handle.

It is yet another object of the invention to simplify the manufacture of bipolar end effectors by reducing the number of insulating components required and by eliminating the need to utilize an adhesive to bond an insulating surface to a metal blade.

These and other objects of the invention are accomplished by the utilization of one ceramic blade having an insulated current conduit proceeding toward the distal end of the blade and therein connecting a conductive strip which proceeds rearward adjacent to the cutting surface of the ceramic blade. The ceramic blade is utilized to cut tissue in conjunction with a metal blade.

DESCRIPTION OF THE PREFERRED EMBODIMENT

Figure 1:
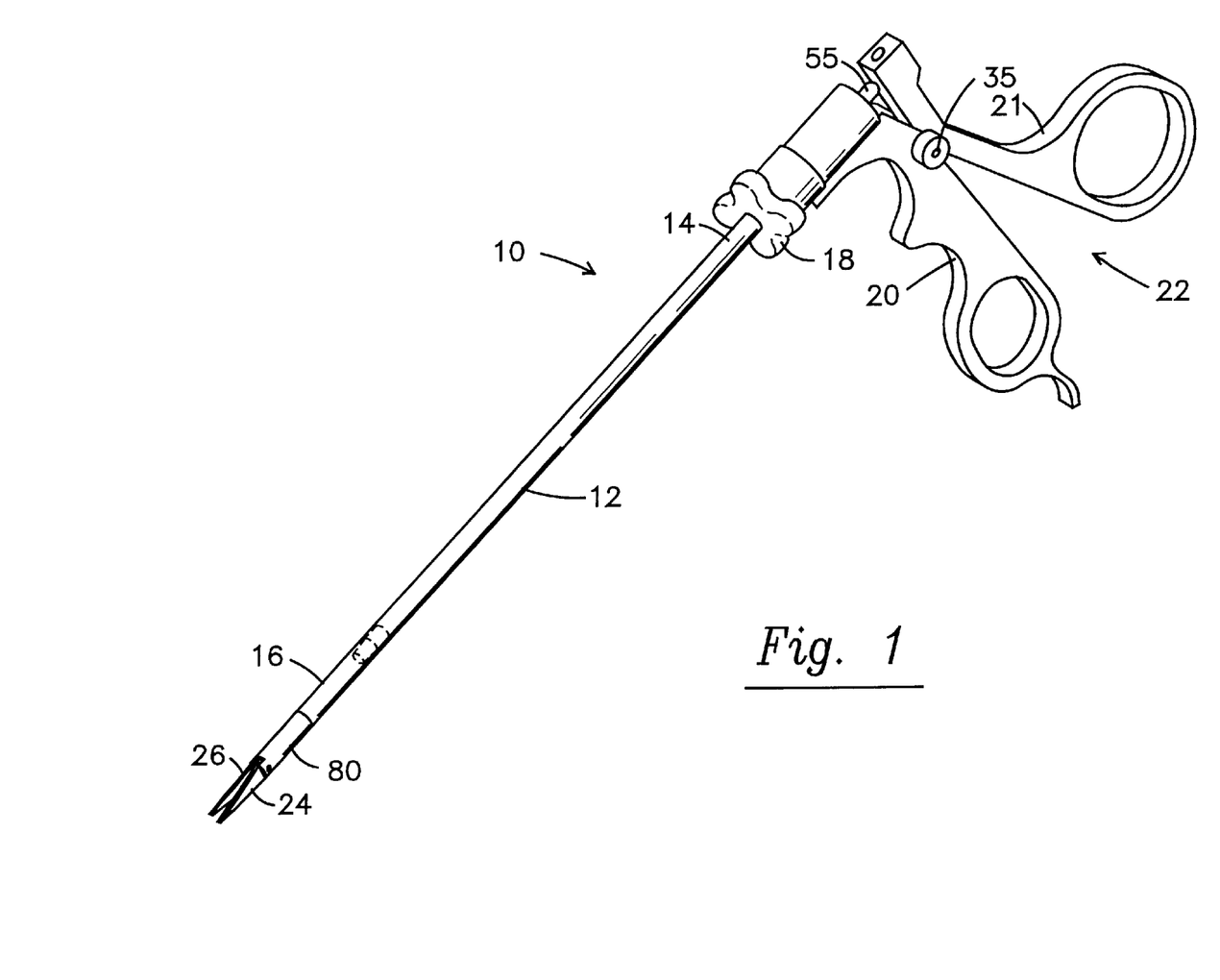
FIG. 1 is a perspective view of an endoscopic electrosurgical scissors constructed in accordance with the present invention.

Referring to FIG. 1, there is indicated generally by numeral 10 a bipolar electrosurgical scissors for endoscopic surgery constructed in accordance with the present invention. It will be understood that the principles of the present invention are equally suitable for use in other bipolar end effector instruments such as graspers and dissectors.

The scissors 10 are seen to include an elongated tubular barrel 12 having a proximal end 14 a distal end 16, and with a lumen extending there between. The outer diameter of the barrel 12 is sufficiently small to be passed through the working lumen of a trocar cannula. Tubular barrel 12 is preferably an insulated metal tube, as by Teflon coating, or a rigid plastic tube. Mounted on the proximal end 14 of the tubular barrel 12 of the bipolar scissors 10 is a knob 18 which facilitates rotation of the tubular barrel 12 and connected end effectors. The tubular barrel 12 and knob 18 are mounted to the stationary portion 20 of an actuator such as handle assembly 22. Manipulation of moveable scissors handle 21 relative to stationary handle section 20 manipulates push rod connector 55 and push rod 50 (illustrated in FIG. 13) which is internal to push rod connector 55 and tubular barrel 12 and in linked communication with end effectors such as blades 24 and 26, which are thereby caused to move in scissors-like action relative to one another.

Figure 6A:
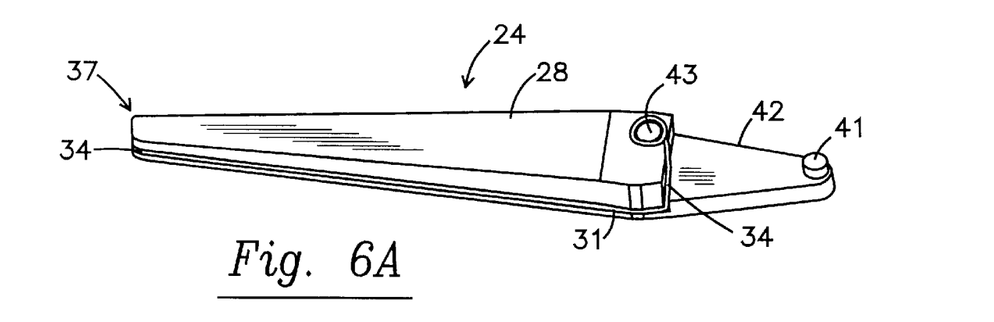
FIG. 6A is a perspective view of a ceramic blade portion according to the present invention.
Figure 6B:
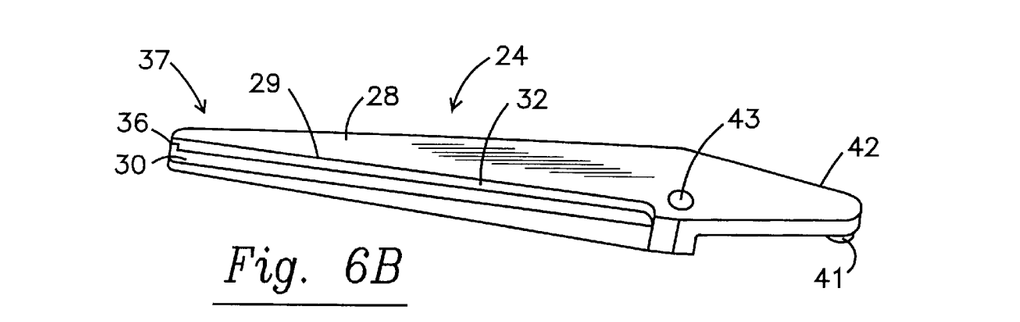
FIG. 6B is a reverse angle view of the ceramic blade portion of FIG. 6A.

Referring to FIG. 6A, an enlarged view of a nonconductive end effector, such as scissors blade 24 is provided. It will be seen that scissors blade 24 is comprised of a nonconductive blade blank 28 which is preferably constructed of a ceramic material such as Zirconia, Mullite, or Alumina available from Coors Ceramics Company, Inc., but which also might be suitably constructed of rigid plastic or insulated metal. At the proximal end 41 of blade 24 is a post 41, a function of which will be explained in connection with cam socket 70 shown in FIG. 12. Proceeding from the post 41 or preferably a surface area on the same side of proximal end 42 of blade 24, perhaps adjacent to aperture 43, is a conductor 34 which proceeds through groove 31 down at least a portion of the end effector, such as blade 24. Preferably, the conductor 34 will proceed to the distal end of the end effector and thereby be connected to the cutting side of the blade 24 as by connection 36, shown in FIG. 6B. Preferably the conductor 34 is insulated as it proceeds distally showing the end effector to connection 36 to prevent inadvertent RF current discharges into tissue. The active side of the end effector, such as the cutting side of blade 24 shown in FIG. 6B has an exposed conductive strip 30 offset from the cutting edge 29 by a short distance of approximately 0.02 inches (0.58 mm). This offset or recess may vary between about 0.003 inches and 0.05 inches to produce a fulgurating gap with metal blade 26 but is preferably between 0.005 inches and 0.030 inches.

Figure 7:
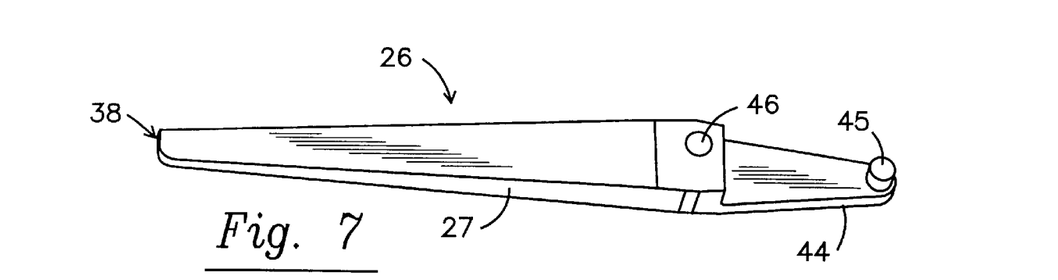
FIG. 7 is a perspective view of a conductive blade portion according to the present invention.

FIG. 7 shows a standard metal scissors blade 26 also having a proximal section 44 with post 45. Blade 26 also has an aperture 46 which corresponds to aperture 43 on the non-conductive blade 24 and is generally manufactured from a traditional metal end effector blank 27. It will be understood that the end effectors may have a variety of shapes and in particular end effectors for scissors may have a curved profile.

Figures 2, 3:
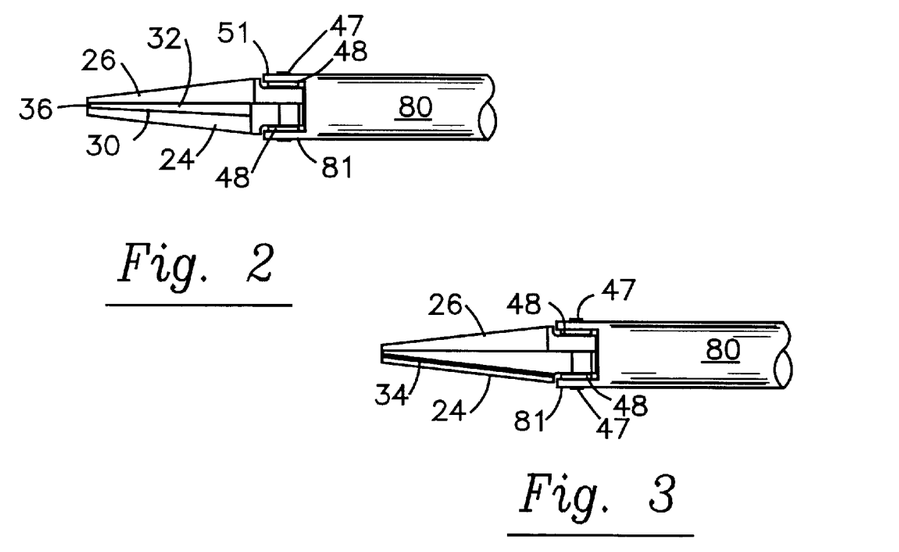
FIG. 2 is a top view of the distal end of a portion of the scissors of FIG. 1.
FIG. 3 is a bottom view of the distal end portion of the scissors of FIG. 1.

FIGS. 2 through 5 show different views of conductive blade 26 and non-conductive blade 24 mounted in clevis section 80. FIG. 2 is a top view showing connecting rivet 47 holding pressure washers 48, conductive blade 26, and non-conductive blade 24, in alignment between clevis wings 81 so that blades 24 and 26 may move in pivotable relation to each other. It will be understood that a single pressure washing 48 may be sufficient. Shown on non-conductive blade 24 is exposed conductive strip 30 offset from cutting edge 29 by gap 32 of approximately 0.02 inches. It will be understood that the fulgurating gap may be adjusted for optimal effect depending upon the design of a particular set of end effectors.

In the bottom plan view of FIG. 3, the conductor 34 is shown. This conductor 34 connects via connection 36 to the exposed conductive strip 30 (shown in FIG. 2). While it is anticipated that the conductor 34 may be plated or press fit into groove 31 and thereafter covered with an insulating resin, it may also be possible to cast the blade 24 from ceramic or plastic with conductor 34 embedded within the blade blank 28.

Figure 4:
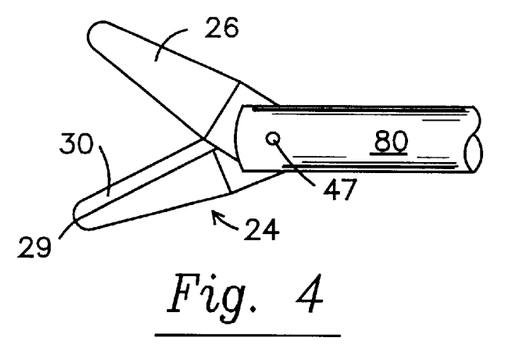
FIG. 4 is a side plan view of the distal end of a portion of the scissors of FIG. 1 in their open position.

FIG. 4 is a left side view showing scissors blade 26 and 24 in their open position. With the cutting side of non-conductive blade 24 exposed, the conductive strip 30 is shown.

Figure 5:
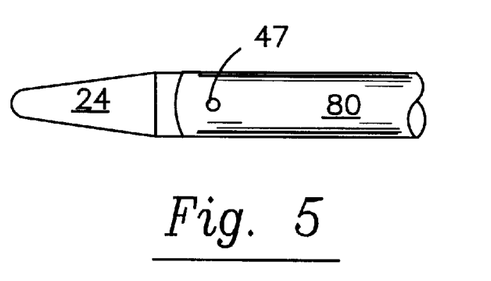
FIG. 5 is a side plan view opposite FIG. 4 of the distal end of a portion of the scissors of FIG. 1 in their closed position.

FIG. 5 shows a right side view with blades 24 and 26 in their closed position so that only non-conductive blade 24 is apparent. It will be understood that while the blades 24, 26 shown in these illustrations have a linear profile when observed from the top as in FIG. 2, the blade profiles could alternatively be arcuate if preferred.

Figures 12, 14:
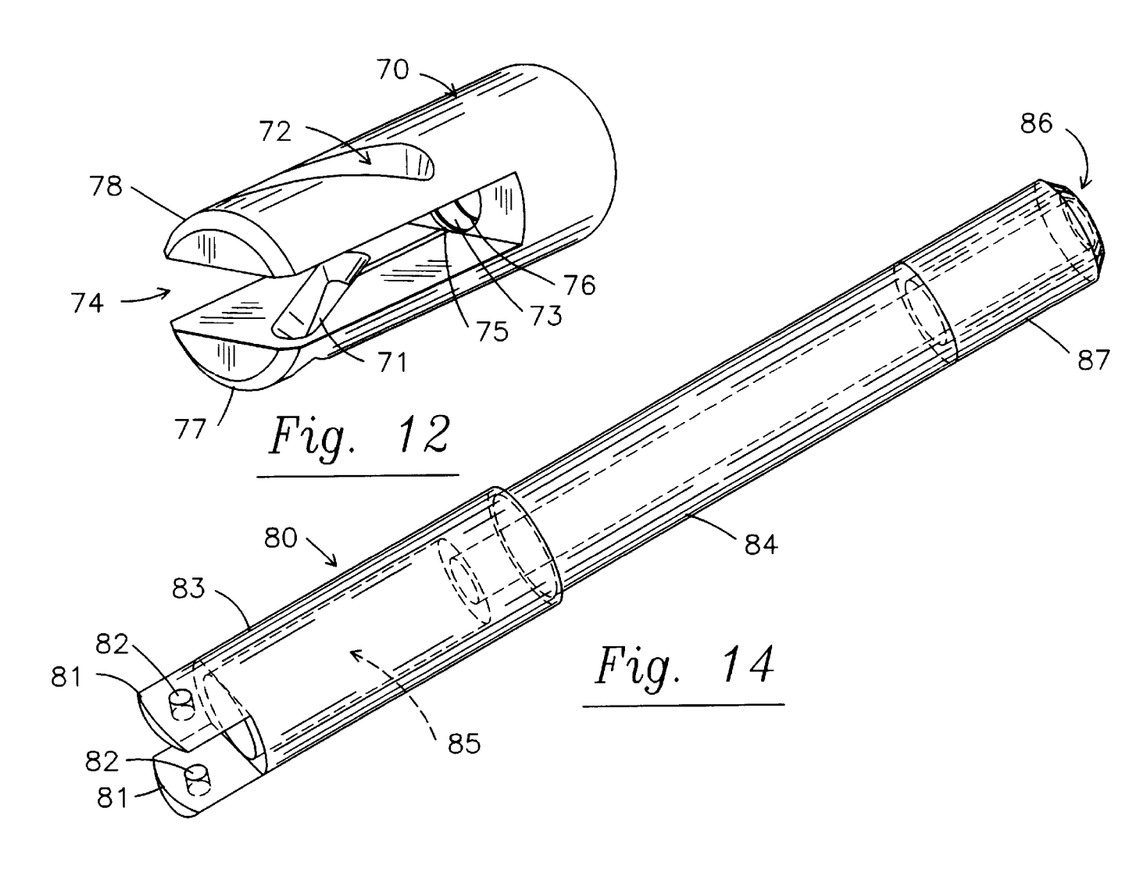
FIG. 12 is a perspective view of a cam part according to the present invention.
FIG. 14 is a perspective view of a clevis section used with bipolar end effectors made according to the present invention.

Turning now to the assembly of bipolar end effectors, non-conductive blade 24 and conductive blade 26 are mounted in cam socket 70 (shown in FIG. 12). First side 77 and opposed side 78 of cam socket 70 define a channel 74 at the distal end of cam socket 70. At the proximal end of cam socket 70 is aperture 73 which contains first connection strip 75 and second connection strip 76 for the purpose of connecting with electrical connections 52, 54 respectively on push rod 50 shown in FIG. 13. It will be understood that the illustrated connection strips 75, 76 are specifically adapted to conduct current to the posts 45, 41 of the blades 24, 26. It will generally be preferred to conduct current to other surfaces on the blades such as adjacent to apertures 43, 46.

In order to secure the blades with their protruding posts 41, 45, the cam socket 70 may be made of a flexible or elastomeric material such as a plastic polymer such as polyurethane that will permit first side portion 70 and second side portion 78 to be bent apart from each other when blades 24, 26 are inserted. Alternatively, the cam socket 70 may be made of rigid material and the blades 24, 26 inserted in a staggered manner and then aligned at the pivot point represented by apertures 43, 46. The post 41 on non-conductive blade 24 is received in groove 71 on the first side 77 of cam socket 70, while post 45 on conductive blade 26 is received in groove 72 on the opposed side 78.

Attached to cam socket 70 by means of chemical, dielectric, or other appropriate bonding, is a conductor from connection strip 75 to first cam socket side 77 so that it may interface with the conductor 34 on the non-cutting side of non-conductive blade 24. Similarly, connective strip 76 is in communication with the second opposed side 78 of cam socket 70 so that an electrical connection can be made with conductive blade 26. This conductor may be embedded within cam socket 70 or may proceed on the exterior surface of cam socket 70 so as not to connect with connective strip 75 on the interior of first side 77.

When blades 24, 26 are mounted in cam socket 70, push rod 50 (shown in FIG. 13) is inserted into aperture 73 so that connector 52 is in contact with connective strip 75 and connector 54 is in contact with connective strip 76. Although push rod 50 may be a relatively small diameter tube containing insulated wires, it is preferably rigid plastic formed with an internal conductor 51 proceeding from connector 52 internal of push rod 50 to proximal end 53. Also, a second or external conductor on push rod 50 proceeds from connector 54 to the proximal end 53 of push rod 50. The assembled blade 24, 26, cam socket 70, and push rod 50 assembly is then inserted between opposed wing sections 81 of clevis section 80. The push rod proceeds through lumen 86 of clevis section 80, while the cam socket 70 is received within chamber 85 of the clevis section 80, and ends 37, 38 of blades 24, 26 are protruding. Apertures 43, 46 on blades 24, 26 respectively (shown in FIGS. 6–7), are aligned with apertures 82 on the clevis section 80, optionally with one or more spring washers 48 (shown in FIGS. 2 and 3) and connected by rivet 47 (shown in FIGS. 2 through 5). If desired, this entire assembly of blades, clevis section, cam socket, and push rod may be disposable.

Figures 10, 11, 13:
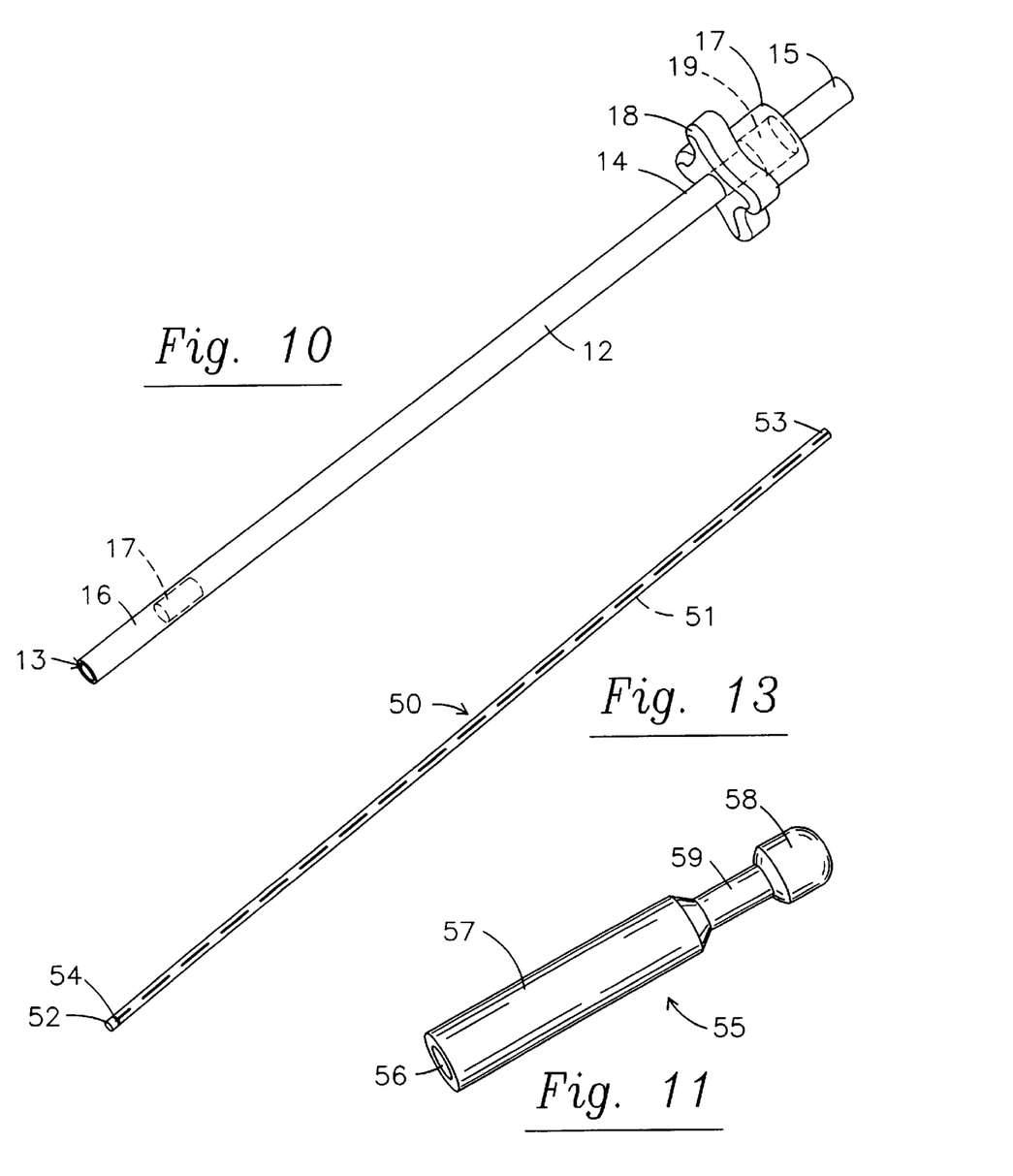
FIG. 10 is a perspective view of an elongated tubular barrel for end effectors having a grasping knob to facilitate rotation.
FIG. 11 is a perspective view of a push rod connector for use in an electrosurgical end effector.
FIG. 13 is a side view of an internal push rod adapted to transmit current or wire connectors through the tubular barrel of an electrosurgical end effector.

Turning now to FIG. 10, the proximal end of push rod 53 is threaded through lumen 13 beginning at the distal end 16 of tubular barrel 12 until it projects at the proximal end 15. When so positioned, the proximal end 87 of clevis section 80 is fixed in mounting section 17 internal to the tubular barrel. Mounting section 17 and proximal clevis section 87 may be press fitted or preferably have mating threads for secure positioning. Relatively narrower section 84 of clevis section 80 is received within the proximal end 16 of tubular barrel 12 while relatively wider section 83 of clevis section 80 protrudes from barrel 12.

Figure 8:
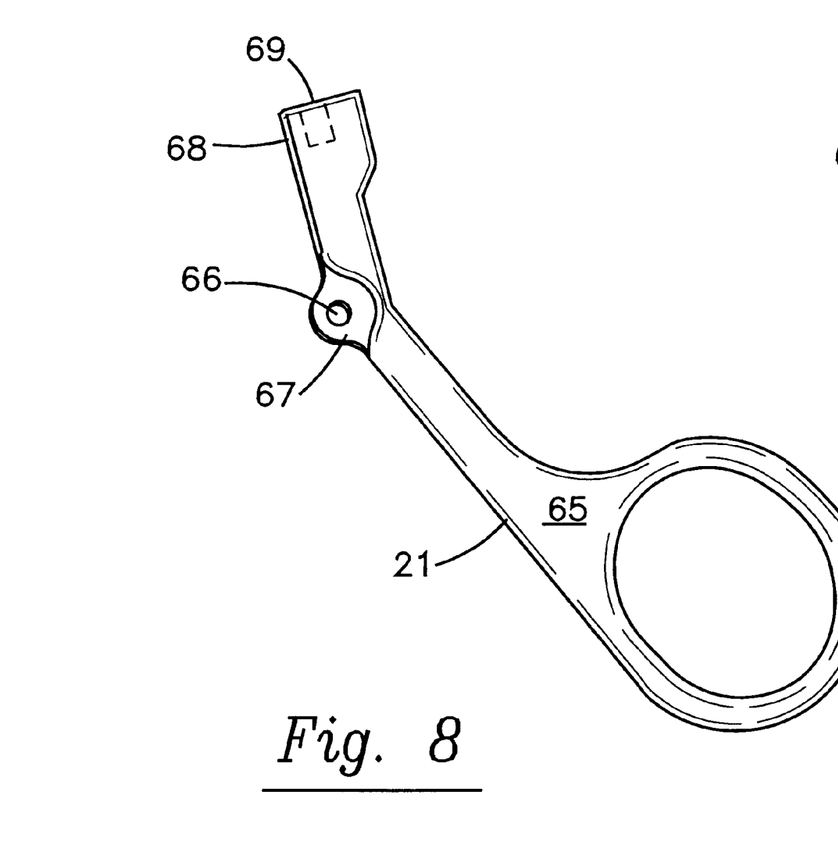
FIG. 8 is a side view of a moveable handle portion for a bipolar end effector.
Figure 9:
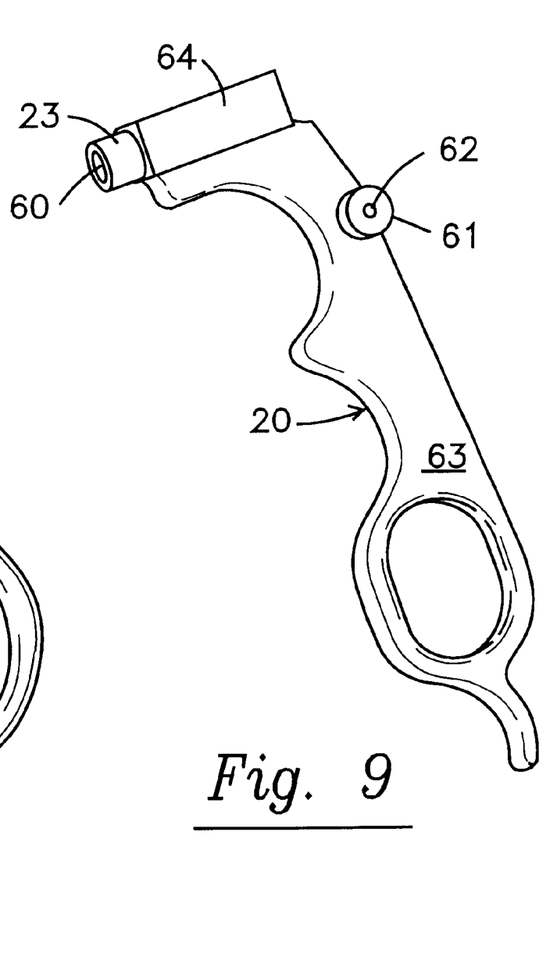
FIG. 9 is a side view of a stationary handle portion for a bipolar end effector.

The next assembly step is for proximal end 15 of tubular barrel 12 to be mounted in aperture 60 of stationary scissors handle 20 (shown in FIG. 9). Protruding fitting segment 23 on stationary handle 20 is in turn received within chamber 19 of tubular barrel assembly 12. The proximal end 53 of push rod 50 protrudes through aperture 60 of stationary handle section 20. Stationary handle 20 has an upper section 64 and a lower handle 63. Also shown is a structure for pivotable attachment with movable handle 21 (shown in FIG. 8) consisting of a clevis like arrangement of two raised circular sections 61 defining between them a gap to receive protruding section 67 on movable handle 21 and each having a threaded aperture 62.

Prior to assembling movable handle section 21 with stationary handle 20, push rod connector 55 is first mounted into the circle and slot configuration 68 of the movable handle 21. Bulbous portion 58 of push rod connector 55 is inserted through the circular section (having a width less than the diameter of bulbous head 58) of opening 68 until the entire bulbous section 58 is internal of movable handle 21 and thereafter push rod connector 55 is slid into the slot section (having a width less than the diameter of bulbous head 58) of opening 68 so that the bulbous head 58 will not pull free. When so positioned, the lumen 56 proceeding through push rod connector 55 is in alignment with an internal two connector plug in communication with external two connector plug 69 at the upper end of movable handle 21.

It should also be noted that aperture 66 of movable handle 21 is sized somewhat larger than aperture 62 on stationary handle 20. The two handle sections 21 and 20 are joined at two points. First, the proximal end 53 of push rod 50 passing through the upper portion 64 of stationary handle section 20 is received through aperture 56 of push rod connector 55 so that it connects through opening 68 into movable handle 21. The proximal end 53 of push rod 50 is thereby placed in electrical connection with tube connector socket 69. The handle sections 20, 21 are also joined by positioning protrusion 67 of moveable handle section 21 in between the clevis like structures 61 on stationary handle 20 and inserting a screw through threaded apertures 62, said screw threads not engaging with the movable scissors handle 21 because of the relatively larger size of aperture 66. This permits free pivoting of the handle sections relative to one another, thereby effecting the pushing or retraction of push end 50 relative to the end effectors.

To utilize bipolar end effectors according to the present invention, plug 69 is connected with appropriate bipolar power source. In use, the positive RF energy proceeds from plug 69 through central electrical connector 51 of push rod 50 to connector 52 at the distal end thereof, and to connective strip 75 of scissors cam socket 70. From connector 70, a current is received by connector 34 on non-conductive blade 24. RF current proceeds along conductor 34 toward the distal end of blade 24 until connection 36 allows the current to communicate with the exposed conductive surface 30. Exposed conductive strip 30 is separated by gap 32 from conductive blade 26. This gap 32 is a space sufficiently narrow to allow RF current to arc through the tissue being held or cut between the non-conductive 24 and conductive 26 end effectors. Because of the gap 32 separating conductive strip 30 from conductive end effector 26, the two end effectors 24 and 26 can touch one another along their entire length as the cutting motion takes place without creating an electrical short circuit between them.

When it is desired to cauterize tissue, the RF voltage is applied to the electrosurgical scissors thereby making the conductive blade 26 and exposed conductive strip 30 the active bipolar electrodes. When the scissors are in contact with tissue, the current flows from a portion of the conductive strip at the cutting point or slightly distal thereto through the tissue to the metal blade 26, thereby effecting cauterization at or just slightly in advance of the cutting point between ceramic blade edge 29 and metal blade 26. To complete the electrical circuit, RF current proceeds through the metal blade 26 to connector 73 on the cam socket 70 which is in contact with connector 54 on push rod 50, which is in turn connected to the negative polarity at connector 69. The design of end effectors in accordance with the invention permits the current to cross before the blades pass one another thereby creating fulguration in advance of the cut and reducing the energy setting required to ensure that the sharply dissected tissue will be provided sufficient RF energy to cauterize.

In heat generating dissection devices the charring of tissue is a common and undesirable side effect. The buildup of charred tissue on electrosurgical devices is common and is typically addressed either by cooling the cutting surfaces of the end effector, as with water, or by using a nonstick surface. Reduced energy settings, as permitted by the present invention, is a solution to the charring and buildup problems. If the RF energy needed to control bleeding is low, the tissue is denatured, and cooked like the white of an egg without burning where the tissue is blanched rather than charred. Tissues are thus sealed and sticking is minimized.

The present invention promotes the efficient use of RF energy by containing the flow of positively charged energy particles through a well defined positive electrode 30 just prior to the tissue cutting point. Some of the current is absorbed to heat the tissue and the remaining positive energy is pulled into the negative electrode 26, thus minimizing the escape of energy from the instrument into surrounding tissues. The novel design focuses the RF energy to reduce the amount of energy required to produce coagulation at the cutting site and to effectively remove the residual energy from the patient's body without affecting other tissues. Lower energy settings result in less char and buildup in the instrument in addition to reducing the likelihood that the energy will affect other tissue or organs.

Alternative electrical connections may be possible that still permit the rotation of barrel 12 upon turning knob 18 without causing a loss of current to the end effectors. The novel cam socket 70 of the present invention obviates the necessity for placing a slot in ceramic blade blank 28 to effect the scissors action. Instead, the ceramic blank 28 is only weakened by a single aperture 43. If multiple holes or substantial slots were cut in ceramic blank 28, it would substantially increase the risk of mechanical failure of the ceramic blank. Accordingly, the present blade post and cam socket design is a substantial improvement over prior art blade design such as those depicted in FIG. 8 of U.S. Pat. No. 5,391,166.

The present invention also obviates the need for utilizing two non-conductive or ceramic surfaces for cutting. This improves the cutting action obtained by the scissors because metal blades are able to provide better and longer cutting performance than ceramic blades. In addition, cauterization occurring slightly forward of the cutting action of the scissors tends to be more effective and minimizes bleeding from the tissue and other described difficulties in utilizing bipolar instruments during surgery.

The electrode surface 30 of the non-conductive blade 24 is designed not to contact the conductive blade 26 and is separated by the fulgurating gap 32 to coagulate tissue. The interference friction between the cutting edge 29 of non-conductive blade 24 does not harm the electrode surface 30 of the non-conductive blade 24 as there is no physical contact or wearing of that conductive surface 30.

Exposure of the positive RF flow from the electrode surface 30 of non-conductive blade 24 to tissue and return through the conductive blade 26 is a unique design to ensure energy flow from the distal end of the end effector toward the proximal end. To ensure this effect, the exposed conductive strip 30 may be selected from an imperfect conductor such as stainless steel or conductive plastics or ceramics in lieu of usual gold plate designs.

Figure 15:
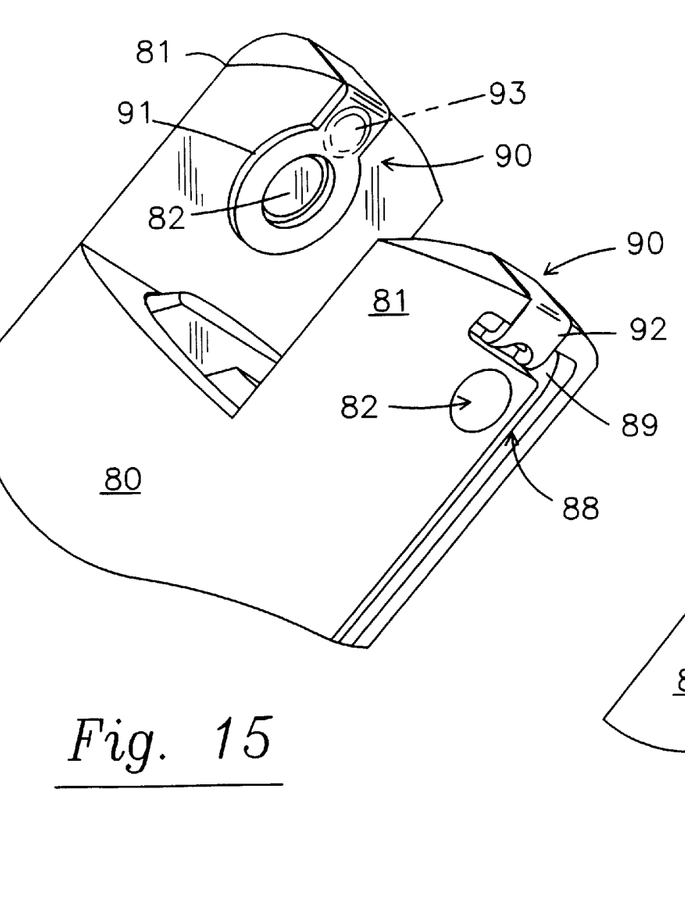
FIG. 15 is a perspective view of the distal end portion of a clevis section showing snap on pressure fittings with the end effectors removed.
Figure 16:
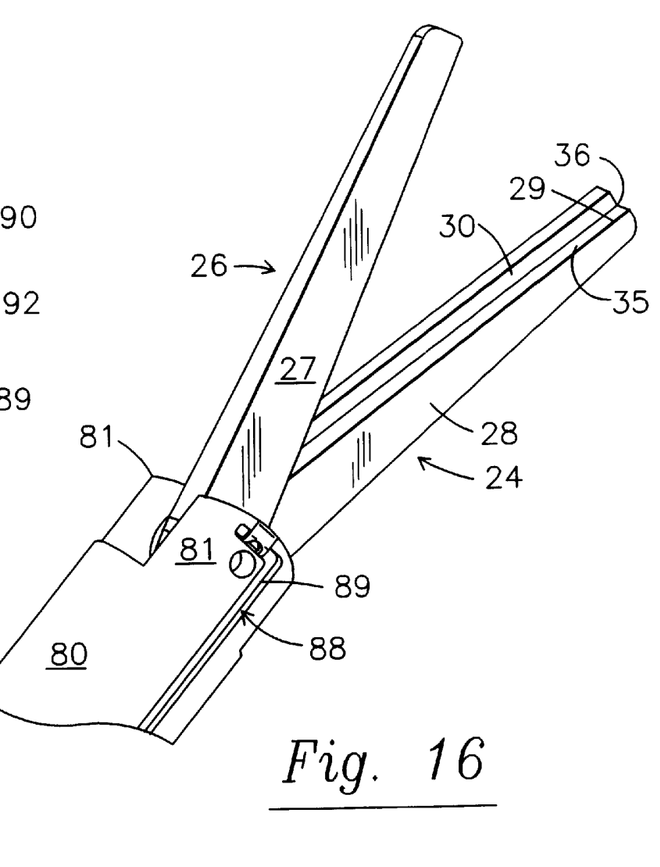
FIG. 16 is a perspective view of the clevis section of FIG. 15 with the end effectors in place.

FIGS. 15 and 16 depict an alternative clevis section 80 design that provides for the current to be conducted in the clevis section rather than the cam socket 70. In this design, current is provided through conductors either in tubular barrel 12 or push rod 50, said conductors being in electrical connection with conductor 89 in slots 88 on opposed sides of clevis section 80. Conduction snap washers 90 mounted on opposed wing sections 81 of clevis section 80 provide conductivity to the blade sections near apertures 43, 46. Snap washers 90 have circular portions 91 mounted surrounding clevis apertures 82, and mounting tabs 92 to hold the washers 90 in place. Dimpled portions 93 bias blades 24, 26 when inserted in clevis section 80 as shown in FIG. 16. This figure also clearly shows the cutting edge 29 of the non-conductive end effector 24, offset from the exposed conductive strip 30 by recess spacer 35 which creates the gap between conductive strip 30 and conductive end effectors 26 when the end effectors 24, 26 are in their closed positions.

The specific embodiment described just by way of explanation rather than limitation in all variations that do not depart from the spirit of the invention are intended to be covered by the appended claims.

What is claimed is:

1. A bipolar surgical instrument comprising first and second interfacing end effectors wherein at least one of said first and second end effectors is pivotable relative to the other on a pivot, and wherein said first end effector is electrically conductive and adapted to be connected to a first pole of a bipolar electrical source, and said second end effector has a proximal end, a distal effector end, an interfacing side, and an opposed side, and comprises:

a non-conductive blank; and a conductor beginning toward the proximal end of said non-conductive blank and proceeding toward the distal effector end and then connecting to an exposed electrode on the interfacing side which proceeds toward the proximal end of said non-conductive blank, said conductor adapted to be connected to a second pole of a bipolar electrical source.

2. The bipolar instrument of claim 1 wherein said second end effector has a cutting edge on its interfacing side.

3. The bipolar instrument of claim 2 wherein the exposed electrode is recessed from the cutting edge by a distance sufficient to create a fulgurating gap when the first electrically conductive end effector is adjacent to the cutting edge.

4. The bipolar instrument of claim 2 wherein the exposed electrode is recessed from the cutting edge by approximately 0.020 inches.

5. The bipolar instrument of claim 1 wherein said first and second end effectors are pivotably mounted in a clevis section.

6. The bipolar instrument of claim 5 wherein said first and second end effectors each have an intermediate aperture and the clevis section has a distal end with two opposed wings and a pin interconnecting said opposed wings and passing through the intermediate apertures of the first and second end effectors.

7. The bipolar instrument of claim 1 wherein said first end effector has a proximal end, a distal effector end, an interfacing side and an opposed side and wherein a post protrudes from the opposed side of the proximal end of each of said first and second end effectors.

8. The bipolar instrument of claim 7 further comprising a cam socket having a proximal end and a distal end, said distal end having a first side portion with a groove defined therein to receive the post protruding from the first end effector, and having a second side portion with a groove defined therein to receive the post protruding from the second end effector.

9. The bipolar instrument of claim 8 wherein said cam socket is received within a clevis section and said first and second end effectors each have an intermediate aperture and the clevis section has a distal end with two opposed wings and a pin interconnecting said opposed wings and passing through the intermediate apertures of the first and second end effectors.

10. The bipolar instrument of claim 9 wherein the clevis section has a first electrical connector in contact with the electrically conductive end effector and a second electrical connector in contact with the conductor of the non-conductive blank.

11. The bipolar instrument of claim 10 wherein said first and second electrical connectors are adapted to be electrically connected to an RF power supply.

12. A bipolar surgical instrument comprising:
(a) an actuator;
(b) a tubular section having a proximal end connected to the actuator and a distal end;
(c) a push rod extending through the tubular section having a proximal end and a distal end;
(d) a cam socket comprising a distal end having a first side portion with a groove defined therein and a second side portion with a groove defined therein and wherein said first and second side portions define a channel;
(e) a first conductive end effector blank having a proximal end and a distal end and an interfacing side and an opposite opposed side and wherein a post protrudes from said opposed side proximal end which is received in the groove defined in the first side portion of the cam socket; said first blank further having an aperture proceeding from the interfacing side to the opposed side intermediate the proximal and distal ends; said first blank adapted to be connected to a first pole of a bipolar power source;
(f) a second non-conductive end effector blank having a proximal end and a distal end and an interfacing side and an opposite opposed side and wherein a post protrudes from said opposed side proximal end which is received in the groove defined in the second side portion of the cam socket, said second end effector blank further comprising:
 (i) an aperture proceeding from the interfacing side to the opposed side intermediate the proximal and distal ends;
 (ii) a conductor proceeding from the proximal end toward the distal effector end; said conductor adapted to be connected to a second pole of the bipolar electrical source;
 (iii) an electrode on the interfacing side in contact with said conductor and proceeding toward the proximal end;
(g) a clevis section having a proximal end encompassing said cam socket and being connected to the distal end of the tubular section and having a distal end defining two opposed clevis wings each having an aligned aperture, said clevis section further comprising a pin received through the aperture of a first clevis wing, the intermediate aperture of the conductive end effector blank, the intermediate aperture of the non-conductive end effector blank, and the aperture of the opposed clevis wing, thereby making said first and second end effector blanks pivotable relative to the other.

13. The bipolar instrument of claim 12 wherein an electrical conductor proceeds from the proximal end of the tubular section to the conductor of the second end effector blank.

14. The bipolar instrument of claim 12 wherein the second non-conductive end effector blank comprises a working surface on the interfacing side that engages with the first end effector blank when the end effector blanks are pivoted.

15. The bipolar instrument of claim 14 wherein the electrode on the interfacing side of the second non-conductive end effector blank is recessed from the working surface by a distance sufficient to create a fulgurating gap.

16. The bipolar instrument of claim 14 wherein the electrode on the interfacing side of the second non-conductive end effector blank is recessed from the working surface by approximately 0.020 inches.

17. The bipolar instrument of claim 15 wherein the working surface is a cutting edge.

18. A method of surgically dissecting and cauterizing tissue comprising the steps of:
(a) connecting a regulated RF power supply to a bipolar surgical scissors having a handle with an actuator; first and second interfacing end effectors wherein at least one of said first and second end effectors is pivotable relative to the other in response to the actuator; wherein said first end effector is electrically conductive and is electrically connected to the RF power supply; and wherein said second end effector has a proximal end, a distal effector end, an interfacing side with a working surface, an opposed side and a conductor commencing toward the proximal end in electrical connection with the RF power supply, and proceeding toward the distal effector end and connecting to an exposed electrode on the interfacing side which proceeds toward the proximal end; and
wherein the working surface of the second end effector contacts the first end effector at least when actuated and the electrode is recessed from the working surface sufficiently to create a fulgurating gap between said electrode and said first end effector;
(b) placing tissue between said first and second end effectors;

(c) selecting the desired RF power output;

(d) utilizing the actuator to cause the first and second end effectors to pivot relative to one another such that the working surface of the second end effector dissects the tissue as it contacts the first end effector;

(e) thereby placing the exposed electrode in sufficient proximity to the tissue and first end effector that RF energy from the power supply proceeds distally along the conductor on the second end effector to the electrode and thereafter proximally towards the contact between the working surface and the first end effector and fulgurating from said electrode to said first end effector at a point no more proximal that the contact between the working surface and the first end effector thereby partially desiccating and cauterizing the tissue distal of the dissection, wherein when the first and second end effectors are interfacing, the electrode is separated from said first end effector by a fulgurating gap of approximately 0.020 inches.

19. The method of claim 18 wherein there is no physical contact between the first end effector and the electrode of the second end effector.

20. A bipolar surgical instrument comprising:

a first electrically conductive end effector adapted to be connected to a first pole of a bipolar power source; and a second end effector interfacing with a pivot relative to said first end effector, the second end effector having a proximal end and a distal effector end, an interfacing side, and an opposed side and comprising a non-conductive blank, a conductor beginning toward the proximal end of the blank extending toward a distal end of the blank and connecting to an exposed electrode on the interfacing side of the blank, said conductor adapted to be connected to a second pole of the bipolar power source;

wherein when the first and second end effectors are interfacing, the electrode is separated from said first end effector by a fulgurating gap of approximately 0.020 inches.

* * * * *